United States Patent [19]

Buckles et al.

[11] 4,012,464
[45] Mar. 15, 1977

[54] S-(2-DIISOPROPYLAMINO-ETHYL)O-ETHYL METHYLPHOSPHONOTHIOATE STABILIZED WITH SOLUBLE CARBODIIMIDES

[75] Inventors: Lawrence C. Buckles, Kingsville, Md.; Stephen M. Lewis, deceased, late of Dugway Proving Ground, Utah; Florence E. Lewis, heir, Long Beach, N.Y.

[73] Assignee: The United States of America as represented by the Secretary of the Army, Washington, D.C.

[22] Filed: Sept. 24, 1965

[21] Appl. No.: 491,074

[52] U.S. Cl. .............................. 260/945; 260/989; 424/211
[51] Int. Cl.² ........................................ C07F 9/165
[58] Field of Search ......................... 260/945, 989

[56] References Cited
FOREIGN PATENTS OR APPLICATIONS 1,058,992  6/1959  Germany ..................... 260/945

*Primary Examiner*—Leland A. Sebastian
*Attorney, Agent, or Firm*—Nathan Edelberg; Robert W. Church

EXEMPLARY CLAIM

1. A composition consisting of S-(diisopropylamino ethyl)O-ethyl methylphosphonothioate, and a stabilizing amount of a soluble carbodiimide selected from the group consisting of dicyclohexylcarbodiimide, diisopropylcarbodiimide, d-o-tolylcarbodiimide, bis(3-chloro-2-methyl-phenyl)carbodiimide, di(p-nitrophenyl)carbodiimide, di-p-tolylcarbodiimide, di(o-chloro-phenyl)carbodiimide, di(o-methoxyphenyl) carbodiimide, and 1 cyclohexyl-3-(2-morpholinoethyl)carbodiimide.

7 Claims, No Drawings

S-(2-DIISOPROPYLAMINO-ETHYL)O-ETHYL METHYLPHOSPHONOTHIOATE STABILIZED WITH SOLUBLE CARBODIIMIDES

This invention described herein may be manufactured and used by or for the Government of the United States of America for governmental purposes without the payment to us of any royalty thereon.

This invention relates to the chemical agent VX, known as S-(2-diisopropylamino ethyl)O-ethyl methylphosphonothioate, and particularly to the stabilization of this agent by adding soluble carbodiimides.

The chemical agent VX, S-(2-diisopropylamino ethyl)O-ethyl methylphosphonothioate $$CH_3 - \overset{\overset{O}{\|}}{\underset{\underset{OC_2H_5}{|}}{P}} - SC_2H_4N(iC_3H_7)_2$$

undergoes a gradual deterioration during storage caused by impurities produced during manufacture. This deterioration was found to be autocatalytic and accelerated by increasing the temperature and also with the presence of rust. It has long been desired to prevent the discarding of large quantities of agent that has deteriorated over any period of shelf life. The impurities normal to VX react extremely fast with the agent producing products capable of causing the agent to have a very short shelf life. It is known that these impurities decompose VX forming products of an objectionable character, usually acidic in nature, which reduce the purity of the agent making it unsuitable for its intended purpose. One of the major mechanisms of the decomposition of the agent is attributed to hydrolysis of the ever present impurity, pyro, which is described below to an acid which in turn reacts with the agent VX producing more of the impurity, pyro, whereby a continuous cyclic process takes place until all of the water has been consumed or the agent has been expanded or reduced to an inoperative purity.

One object of this invention is to produce stable VX having a long shelf life.

Another object of this invention is to eliminate the daily preparation of the chemical agent VX.

A further object is the prevention of the agent VX from reacting with the impurities normal to the agent.

The object of this invention is the provision of novel stabilizers for VX, which stabilizers are effective when present in relatively small quantities.

Other objects of this invention will be apparent from the following detailed description and claims.

We have found that numerous compounds hereinafter set forth are effective stabilizers for the chemical agent VX. Advantageously the stabilizers, carbodiimides, are soluble in the liquid chemical agent VX, without discoloring or significantly increasing the odor of the liquid agent.

The present storage criterion for VX is that it deteriorates no more than 20% in six months storage in steel at 71° C. The unstabilized stored VX degrades 10% in approximately two months and 20% in approximately 3.3 months. Thus, it is determined that the VX without a stabilizer is unacceptable. However, by the addition of 2% stabilizer, such as dicyclohexylcarbodiimide, the VX has decreased 10% in purity in 3.3 months and 20% in seven months. Therefore, by the addition of a stabilizer, carbodiimide, the VX is made acceptable. The addition of a 6% by weight of a carbodiimide yields a stabilized VX having a 10% decrease in purity in nine months at 71° C. However, for shelf life of several years at ambient temperature, the stabilizing agent need only be present in amounts of 2-4% by weight.

The carbodiimides employed as stabilizers may be selected from diisopropyl carbodiimide, di-o-tolylcarbodiimide, bis(3-chloro-2-methylphenyl)carbodiimide, di(p-nitrophenyl)carbodiimide, di-p-tolylcarbodiimide, di(o-methoxyphenyl)carbodiimide, di(o-chlorophenyl)carbodiimide, 1 cyclohexyl-3-(morpholinoethyl)carbodiimide, and N,N'dicyclohexylcarbodiimide. Excellent results have been obtained when using N,N'dicyclohexylcarbodiimide as a stabilizer for VX.

The chemical agent VX undergoes a gradual deterioration during storage. This deterioration is found to be autocatalytic and accelerated by impurities normal to VX. Furthermore, the deterioration of the agent VX is accelerated by the presence of rust and increase of temperature. The impurities present in VX, S-(2-diisopropylaminoethyl)O-ethyl methylphosphonothioate, $$CH_3 - \overset{\overset{O}{\|}}{\underset{\underset{OC_2H_5}{|}}{P}} - SC_2H_4N(iC_3H_7)_2$$

are thiolamine, β-diisopropylaminoethanethiol $$HS - CH_2 CH_2 N (iC_3H_8)_2$$

p-diethyldimethylpyrophosphonate, hereinafter designated as pyro $$CH_3 - \overset{\overset{O}{\|}}{\underset{\underset{OC_2H_5}{|}}{P}} - O - \overset{\overset{O}{\|}}{\underset{\underset{OC_2H_5}{|}}{P}} - CH_3$$

phosphonic acid, ethyl methylphosphonic acid, $$CH_3 - \overset{\overset{O}{|}}{\underset{\underset{OC_2H_5}{|}}{P}} - OH$$

alcohols and water. All of the impurities normal to VX except pyro, contain reactive hydrogen atoms. Therefore, it was decided to employ compounds such as carbodiimides which are known to react with active hydrogen containing compounds such as alcohols, acids, water and thiols. These stabilizing compounds react faster with the reactive hydrogen atoms of the normal impurities, producing products which themselves will not attack the VX molecule. This prompt reaction prevents the deterioration of VX by eliminating the impurities and thus enabling the chemical agent to be stored for an extended period of time. Furthermore, the reaction product produced after adding the carbodiimide stabilizer results in an irreversible reaction. The compounds employed as stabilizers fail to react with the chemical agent VX or generate a pressure within the system by the evolution of a gas.

The proportions of carbodiimides employed as stabilizers may be rather small. For example the quantity of compound used may be within the range of 2.0% to 10.0% by weight of the chemical agent VX. The carbodiimide is found to be an excellent stabilizer at 2% by weight and at 71° C for extremely long periods of storage.

In the case whereby the impurity water reacts with the impurity pyro, phosphonic acid is produced which in turn attacks the agent VX producing more pyro. As can be seen, this is a continuous cyclic process until the agent is placed in an undesirable and unuseable purity and/or until all the water is consumed. The impurity pyro is harmful only in the presence of water.

$$\text{pyro} + H_2O \longrightarrow \text{phosphonic acid}$$

$$\text{phosphonic acid} + VX \longrightarrow \text{pyro}$$

Therefore, the impurities normal to VX particularly water must be removed from the agent in order that the agent will retain a purity within the criteria established for the agent VX. The stabilizing agents, carbodiimides, form an irreversible reaction with the impurities in VX, react with the impurities of VX producing products that do not react with the molecule VX and thus eliminate the obstacle, deterioration, permitting the agent to be stored for an extended period of time.

The rate of decomposition of the chemical agent VX, is dependent upon the impurities present. The mechanisms of decomposition of VX by the impurities water, acids, thiols and alcohols are the most deleterious. The agent VX reacts with water to produce an acid RO(-R')P(O)OH and thiol (RSH). The acid further reacts with another mole of VX to produce the the pyro ester $$\begin{array}{cc} O & O \\ \| & \| \\ (R-P-O-P-R) \\ | & | \\ OR' & OR' \end{array}$$

and another mole of thiol. In the presence of thiol, VX reacts more rapidly to produce the biologically inactive decomposition product — bis compound which has the formula:

$$\begin{array}{c} O \\ \| \\ CH_3-P = [S-C_2H_4-N(iC_3H_7)_2] \end{array}$$

Each one of these degradation reactions, therefore, regenerates more impurities to further the decomposition process.

The carbodiimides such as dicyclohexylcarbodiimide do not stabilize the VX molecule by addition or complexing but instead react faster than the VX with the normal impurities, thus preventing those impurities from attacking the VX molecule.

The carbodiimides react with the impurities normal to VX producing area analogs which do not react with the chemical agent VX. Thus the agent VX is able to remain stable for long periods of time or is prevented from deteriorating by eliminating the various normal impurities. For instance, N,N'-dicyclohexylcarbodiimide reacts with water to produce N,N'-dicyclohexyl urea which is inert in the presence of the chemical agent VX.

When the stabilizers of this invention are present in the chemical agent VX, the biologic potency as applied to the percutaneous application to mice and rabbits is not decreased and in some cases increased by the addition of this stabilizer to VX.

The tests of materials hereinbefore set forth are by way of example only, and are not to be taken as limiting the invention which includes the use of all those compounds disclosed, as inhibitors for deterioration of the agent VX. It is to be understood that the foregoing detailed description is given merely by way of illustration and that many variations may be made therein without departing from the spirit of our invention.

EXAMPLE I

Storage of VX plus Dicyclohexylcarbodiimide Stored in Steel Cups at 71° C

| Time (months) at 71° C | Stabilizer % by wt. | Purity Before Storage % | Purity After Storage % | Decrease in Purity |
|---|---|---|---|---|
| 5 | 0 | 94.5 | 24.1 | 70.4 |
| 5 | 0 | 92.0 | 19.3 | 72.7 |
| 5 | 2.0 | 90.5 | 76.8 | 13.7 |
| 5 | 2.2 | 90.0 | 79.7 | 10.3 |
| 5 | 4.0 | 88.9 | 81.6 | 7.3 |
| 5 | 4.3 | 88.4 | 78.1 | 10.3 |

EXAMPLE II

Storage of VX plus Diisopropylcarbodiimide Stored in Steel Cups at 71° C

| Time (months) at 71° C | Stabilizer % by wt. | Purity Before Storage % | Purity After Storage % | Decrease in Purity |
|---|---|---|---|---|
| 5 | 0 | 94.5 | 24.1 | 70.4 |
| 5 | 0 | 92.0 | 19.3 | 72.7 |
| 5 | 1.1 | 92.0 | 74.4 | 17.6 |
| 5 | 2.0 | 91.3 | 74.4 | 16.9 |
| 5 | 2.3 | 88.6 | 74.3 | 14.3 |
| 5 | 4.0 | 87.7 | 67.7 | 20.0 |

EXAMPLE III

Storage of VX plus Dicyclohexylcarbodiimide Stored in Aluminum Cups at 71° C

| Time (months) at 71° C | Stabilizer % by wt. | Purity Before Storage % | Purity After Storage % | Decrease in Purity |
|---|---|---|---|---|
| 5 | 0 | 90.6 | 67.4 | 23.2 |
| 5 | 3.1 | 85.2 | 77.6 | 7.6 |
| 6 | 1.8 | 88.5 | 80.9 | 7.6 |
| 6 | 3.1 | 87.5 | 83.4 | 4.1 |
| 6 | 6.2 | 84.8 | 77.9 | 6.9 |

EXAMPLE IV

Storage of VX plus Diisopropylcarbodiimide Stored in Aluminum Cups at 71° C

| Time (months) at 71° C | Stabilizer % by wt. | Purity Before Storage % | Purity After Storage % | Decrease in Purity |
|---|---|---|---|---|
| 5 | 0 | 90.6 | 67.4 | 23.2 |
| 5 | 2.5 | 85.2 | 78.6 | 6.6 |
| 6 | 1.2 | 91.3 | 84.2 | 7.1 |
| 6 | 2.5 | 88.3 | 84.0 | 4.3 |

-continued

Storage of VX plus Diisopropylcarbodiimide Stored in Aluminum Cups at 71° C

| Time (months) at 71° C | Stabilizer % by wt. | Purity Before Storage % | Purity After Storage % | Decrease in Purity |
|---|---|---|---|---|
| 6 | 2.5 | 86.8 | 78.8 | 8.0 |

EXAMPLE V

Storage of VX plus Carbodiimides Stored in Steel at 71° C

| Storage | | VX (untreated) | Sample | | | |
|---|---|---|---|---|---|---|
| | | | VX plus dicyclohexyl-carbodiimide | | VX plus diisopropyl-carbodiimide | |
| Time Mo. | Temp. °C | % | 3% % by wt. | 7% % by wt. | 3% % by wt. | 7% % by wt. |
| 3 | 0 | 86.1 | 84.7 | 79.3 | 84.0 | 77.8 |
| 1 | 71 | 60.8 | — | — | — | — |
| 2 | 71 | 76.1 | — | — | — | — |
| 3 | 71 | 43.3 | 76.5 | 77.1 | 76.8 | 74.3 |

EXAMPLE VI

VX plus 10% Dicyclohexylcarbodiimide Stored in Steel at 71° C

| Length of Storage Mo. | VX Purity | |
|---|---|---|
| | Untreated Sample % | Sample plus Stabilizer % |
| 0 | 85.5 | 77.0* |
| 1 | 71.1 | 71.6 |
| 2 | 66.8 | 69.3 |
| 3 | 54.0 | 64.1 |
| 6 | 40.4 | 62.7 |

*Calculated value based on the dilution by the additive.

Having described our invention what we desire to secure by Letters Patent is:

1. A composition consisting of S-(diisopropylamino ethyl)O-ethyl methylphosphonothioate, and a stabilizing amount of a soluble carbodiimide selected from the group consisting of dicyclohexylcarbodiimide, diisopropylcarbodiimide, d-o-tolylcarbodiimide, bis(3-chloro-2-methyl-phenyl)carbodiimide, di(p-nitrophenyl)carbodiimide, di-p-tolylcarbodiimide, di(o-chlorophenyl)carbodiimide, di(o-methoxyphenyl)carbodiimide, and 1 cyclohexyl-3-(2-morpholinoethyl)-carbodiimide.

2. A composition consisting of S-(diisopropylamino ethyl)O-ethyl methylphosphonothionate, and a soluble carbodiimide, said carbodiimide selected from the group consisting of dicyclohexylcarbodiimide, diisopropylcarbodiimide, d-o-tolylcarbodiimide, bis(3-chloro-2-methyl-phenyl)carbodiimide, di(p-nitrophenyl)carbodiimide, di-p-tolylcarbodiimide, di(o-chlorophenyl)carbodiimide, di(o-methoxyphenyl)carbodiimide, and 1 cyclohexyl-3-(2-morpholinoethyl)-carbodiimide being present in amounts between 2.0% to 10.0% by weight of said agent.

3. A composition consisting of S-(diisopropylamino ethyl)O-ethyl methylphosphonothioate, and a stabiizing amount of a soluble carbodiimide selected from the group consisting of dicyclohexylcarbodiimide, diisopropylcarbodiimide, d-o-tolylcarbodiimide, bis(3-chloro-2-methyl-phenyl)carbodiimide, di(p-nitrophenyl)carbodiimide, di-p-tolylcarbodiimide, di(o-chlorophenyl)carbodiimide, di-o-methoxyphenyl)carbodiimide, and 1 cyclohexyl-3-(2-morpholinoethyl)-carbodiimide, said stabilizer being present in an amount greater than 2% by weight of said agent.

4. A composition consisting of S-(diisopropylamino ethyl)O-ethyl methylphosphonothioate, and a stabilizing amount of N,N'-dicyclohexylcarbodiimide, said stabilizer being present in an amount of 2% by weight of said agent.

5. A composition consisting of S-(diisopropylamino ethyl)O-ethyl methylphosphonothioate, and a stabilizing amount of N,N'-dicyclohexylcarbodiimide, said stabilizer being present in an amount of 4% by weight of said agent.

6. A composition consisting of S-(diisopropylamino ethyl)O-ethyl methylphosphonothioate, and a stabilizing amount of N,N'-dicyclohexylcarbodiimide.

7. A composition consisting of S-(diisopropylaminoethyl)O-ethyl methylphosphonothioate and 2% to 10% by weight of N,N'-dicyclohexylcarbodiimide.

* * * * *